United States Patent [19]

Renner

[11] Patent Number: 4,728,742
[45] Date of Patent: Mar. 1, 1988

[54] SUBSTITUTED, UNSATURATED, BICYCLIC IMIDES CONTAINING HYDROXYL GROUPS, AND POLYMERS THEREOF

[75] Inventor: Alfred Renner, Muntelier, Switzerland

[73] Assignee: Ciba-Geigy Corporation, Ardsley, N.Y.

[21] Appl. No.: 746,428

[22] Filed: Jun. 19, 1985

[30] Foreign Application Priority Data

Jun. 27, 1984 [CH] Switzerland .................. 3095/84

[51] Int. Cl.$^4$ ........................................ C07D 209/44
[52] U.S. Cl. ................................. 548/435; 528/117
[58] Field of Search .................. 548/435, 513, 514; 528/117

[56] References Cited

U.S. PATENT DOCUMENTS

| | | | |
|---|---|---|---|
| 3,105,839 | 10/1963 | Renner | 549/237 |
| 3,450,711 | 6/1969 | Megna et al. | 548/513 |
| 4,193,927 | 3/1980 | Baumann et al. | 548/513 |
| 4,225,498 | 9/1980 | Baudouin et al. | 548/435 |
| 4,278,780 | 7/1981 | Nishikawa et al. | 528/117 |
| 4,283,521 | 8/1981 | Jones | 528/117 |
| 4,414,269 | 11/1983 | Lubowitz et al. | 548/435 |
| 4,510,272 | 4/1985 | Loszewski | 528/117 |
| 4,515,962 | 5/1985 | Renner | 548/435 |
| 4,579,916 | 4/1986 | Schmid et al. | 528/17 |
| 4,587,317 | 5/1986 | Renner | 526/259 |
| 4,604,437 | 8/1986 | Renner | 526/262 |

FOREIGN PATENT DOCUMENTS 105024 4/1984 European Pat. Off. .......... 548/435

Primary Examiner—Mary E. Ceperley
Attorney, Agent, or Firm—Harry Falber

[57] ABSTRACT

Imides of the formula I

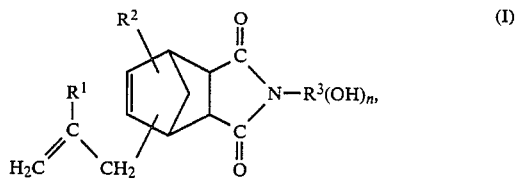

wherein $R^1$, $R_2$, $R^3$ and n have the meanings defined in claim 1, are intermediates for producing polymers having excellent physical properties, and for producing sulfonic acid esters.

13 Claims, No Drawings

SUBSTITUTED, UNSATURATED, BICYCLIC IMIDES CONTAINING HYDROXYL GROUPS, AND POLYMERS THEREOF

The invention relates to bicyclo [2.2.1]hept-5-ene-2,3-dicarboxylic acid imides containing hydroxyl groups and substituted by allyl or methallyl and, if appropriate, by methyl, to the production thereof, and to the polymers obtainable therefrom, in the presence or absence of other comonomers.

Maleinimides and bismaleinimides as well as N-allyl-monomaleinimides are known.

The U.S. Pat. No. 3,450,711 concerns bisimide compounds produced by reaction of endo,cisbicyclo[2.2.1-]hept-5-ene-2,3-dicarboxylic anhydride (=5-norbornene-2,3-dicarboxylic anhydride) with selected organic diamines. These bisimides contain neither methyl substitutents nor methallyl or allyl substituents in the imide radical, and differ from the present compounds both on account of their structure and on account of their chemical reactivity. The compounds according to this U.S. patent are used as intermediates for producing epoxide compounds.

The European Patent Application No. 0,105,024 describes allyl- or methallyl-substituted bicyclo[2.2.1-]hept-5-ene-2,3-dicarboxylic acid imides and the polymers obtainable therefrom.

The substituted bicyclo[2.2.1]hept-5-ene-2,3-dicarboxylic acid imides containing hydroxyl groups according to the invention are valuable starting products, both for polymers having excellent properties, and for sulfonic acid esters derived therefrom. They are characterised by the following formula I:

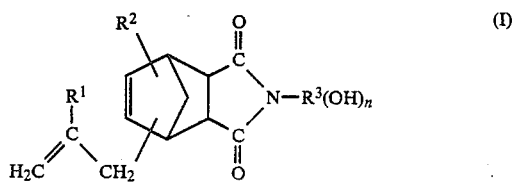

(I)

wherein $R^1$ and $R^2$ independently of one another are each hydrogen or methyl, n is 1, 2 or 3, and $R^3$ is a direct bond, or a $C_2$–$C_{20}$-aliphatic radical which can be interrupted in the chain by O atoms, a mono- or polynuclear $C_5$–$C_{20}$-cycloaliphatic radical or a $C_6$–$C_{20}$-aromatic radical, or a group of the formula II

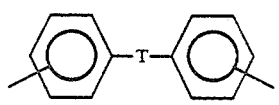

(II)

wherein T is methylene, isopropylidene, CO, O, S or $SO_2$, the OH groups being bound to different C atoms or $R^3$.

$R^1$ and $R^2$ are preferably each a hydrogen atom.

$R^3$ can be a di- to tetravalent, straight-chain or branched-chain, aliphatic radical having 2–20, preferably 2–12, and particularly 2–6, C atoms, which can be interrupted in the chain by one or more oxygen atoms. Examples of suitable aliphatic radicals $R^3$ are: ethylene, 1,2- and 1,3-propylene, butylene, penta- and hexamethylene, heptylene, octylene, decylene, dodecylene, hexadecylene or neopentylene, as well as radicals of glycerol, of 1,1,1-tris(hydroxymethyl)propane and of pentaerythritol(2,2-bis(hydroxymethyl)-1,3-propanediol).

Aliphatic radicals interrupted by oxygen atoms can be derived for example from ethylene glycol or propylene glycol, and can correspond to groups of the formulae —$CH_2CH_2[OCH_2CH_2]_{\overline{m}}$ or —$CH_2CH_2CH_2[OCH_2CH_2CH_2]_{\overline{m}}$, m being 1–10.

$R^3$ can also be a mono- or polynuclear, cycloaliphatic, especially divalent, radical having 5–20 C atoms, for example cyclopentylene, cyclohexylene, cycloheptylene, cyclooctylene, bis(cyclohexylene)methane, 2,2-bis(cyclohexylene)propane and decalinylene.

When $R^3$ is an aromatic radical, it denotes preferably divalent radicals, for example 1,3- or 1,4-phenylene or naphthylene, which can in each case if desired also be substituted by one or more $C_1$–$C_4$-alkyl groups, such as methyl, ethyl or propyl. The stated groups are preferably unsubstituted. Particularly preferred aromatic radicals are 1,3- and 1,4-phenylene groups.

If $R^3$ is a group of the formula II, the symbol T is preferably O, $SO_2$ and especially methylene or isopropylidene.

Particularly preferred compounds of the formula I are those wherein $R^3$ is a direct bond, groups —$C_rH_{2r}$— in which r is 2–6, —$CH_2CH_2[OCH_2CH_2]_{\overline{m}}$ in which m is 2 and especially 1, a radical of glycerol, a mononuclear, divalent, cycloaliphatic radical having 5–8 C atoms, such as cyclopentylene and cyclohexylene, an unsubstituted divalent $C_6$–$C_{10}$-aromatic radical, such as 1,3- and 1,4-phenylene or naphthylene, or a group of the formula II in which T is O, $SO_2$ and in particular methylene or isopropylidene.

More especially preferred compounds of the formula I are those wherein $R^3$ is a direct bond, or the radical

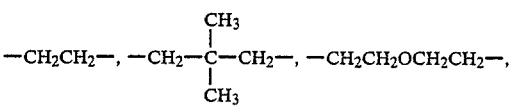

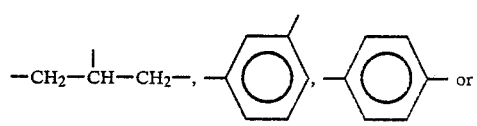

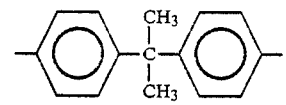

Most preferred compounds of the formula I are those wherein $R^3$ is a direct bond, ethylene or 1,4-phenylene.

The imides according to the invention can be produced, in a manner known per se, for example by reaction of an anhydride of the formula III

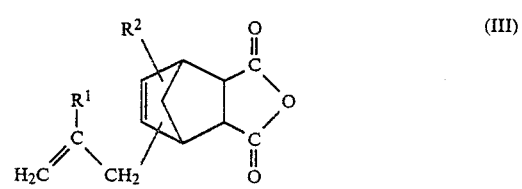

(III)

with a compound of the formula IV

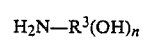

(IV), wherein $R^1$, $R^2$, $R^3$ and n have the meanings defined under the formula I, at elevated temperature, and with the removal by distillation of the water forming during the reaction. When the compounds of the formula IV are low-boiling compounds, it is advisable to use an excess of these reactants. The reaction can be performed without solvent, or in the presence of an inert solvent applicable for the azeotropic removal of water (entraining agent). The temperature of the reaction can be between 100° and 250° C. The imides of the formula I are preferably produced in the melt under a pressure of at most 4500 Pa at a temperature of between 130° and 220° C., particularly between 180° and 220° C.

Compounds of the formula IV surprisingly react just as well with anhydrides of the formula III as do OH-free amines, and do not result in product mixtures caused by reactions of the hydroxyl group. The starting materials of the formula III can be produced, using the process described in the U.S. Pat. No. 3,105,839, by reacting sodium cyclopentadienide or sodium methylcyclopentadienide with an allyl or methallyl halide, upon which follows a Diels-Alder reaction with maleic anhydride. Although it is stated in the U.S. patent that the allyl group is bound in the 7-position of the bicyclic system, more recent investigations show that an isomeric mixture, with respect to the position of the allyl group (in the 1- and 6-position) and also with respect to the endo- and exo-configuration of the anhydride moiety, is formed. It was only possible hitherto to isolate the isomeric components by preparative gas-chromatography.

Compounds of the formula IV are known or can be produced by processes known per se.

The compounds according to the invention are liquid or low-melting solid substances, which can be polymerised into solid products having a high glass transition temperature.

Owing to the presence of two different reactive groups, of the double bonds as well as of the hydroxyl groups, the imides according to the invention can be used as educts or intermediates for the production of different polymers. The imides of the formula I can thus be reacted for example with polyesters having carboxyl terminal groups, with polyisocyanates or with polybutadienes.

The imides of the formula I can be used also as monomers or comonomers for producing novel polymers. The reaction can be performed for example by heating for 6-60 hours at a temperature of between 180° and 300° C., preferably between 200° and 250° C. With regard to the preferred meanings of $R^1$, $R^2$, $R^3$ and n, the aforementioned definitions apply.

The compounds according to the invention can be used directly and be polymerised or condensed, or they can be firstly dissolved in an organic solvent, such as toluene, xylene, methyl ethyl ketone, ethylene glycol monoalkyl and -dialkyl ethers having 1-4 C atoms in the alkyl groups, or in a similar solvent customarily used in the lacquer industry. Solutions of this type can serve as impregnating agents or coating agents, and also as dispatch objects for the consumer.

A preferred field of application of the imides according to the invention is their reaction with epoxide resins, whereby cured products having excellent properties are obtained.

The present Application thus relates also to curable mixtures containing imides of the formula I, epoxide resins and, if necessary, further customary additives, for example catalysts (curing accelerators). Further subject matter of the invention are polymers which are obtainable by reacting imides of the formula I with epoxide resins, preferably in the presence of a catalyst. Imides preferably used are N-hydroxyaryl derivatives according to the invention.

The epoxide resins to be used preferably have on average more than one epoxide group per molecule. There may be mentioned in particular:

alicyclic polyepoxides, such as epoxyethyl-3,4-epoxycyclohexane (vinylcyclohexenediepoxide), limonenediepoxide, dicyclopentadienediepoxide, bis(3,4-epoxycyclohexylmethyl)adipate, 3',4'-epoxycyclohexylmethyl-3,4-epoxycyclohexanecarboxylate, 3',4'-epoxy-6'-methylcyclohexylmethyl-3,4-epoxy-6-methylcyclohexanecarboxylate, 3-(3',4'-epoxycyclohexyl)-2,4-dioxaspiro[5,5]-8,9-epoxyundecane and 3-glycidyloxyethoxyethyl-2,4-dioxaspiro[5,5]-8,9-epoxyundecane;

di- or polyglycidyl ethers of polyhydric alcohols, such as 1,4-butanediol or polyalkylene glycols, such as polypropylene glycols, di- or polyglycidyl ethers of cycloaliphatic polyols, such as 2,2-bis(4'-hydroxycyclohexyl)propane, di- or polyglycidyl ethers of polyvalent phenols, such as resorcinol, bis(4-hydroxyphenyl)methane (bisphenol-F), 2,2-bis(4'-hydroxyphenyl)propane (bisphenol-A), 2,2-bis(4'-hydroxy-3',5'-dibromophenyl)propane, 1,1,2,2-tetrakis(4'-hydroxyphenyl)ethane, or condensation products of phenols with formaldehyde, obtained under acidic conditions, such as phenol novolaks and cresol novolaks, and also di- or poly($\beta$-methylglycidyl)ethers of the above-mentioned polyalcohols and polyphenols;

polyglycidyl esters and poly($\beta$-methylglycidyl)esters of polyvalent carboxylic acids, such as phthalic acid, terephthalic acid, tetrahydrophthalic acid and hexahydrophthalic acid; and N-glycidyl derivatives of amines, amides and heterocyclic nitrogen bases, such as N,N-diglycidylaniline, N,N-diglycidyltoluidine, N,N,N',N'-tetraglycidylbis(4-aminophenyl)methane, triglycidylisocyanurate, N,N'-diglycidylethylurea, N,N'-diglycidyl-5,5-dimethylhydantoin, N,N'-diglycidyl-5-isopropylhydantoin and N,N'-diglycidyl-5,5-dimethyl-6-isopropyl-5,6-dihydrouracil.

Polyglycidyl ethers of phenol- or cresol-formaldehyde novolaks as well as diglycidyl ethers of bisphenol-A and bisphenol-F are particularly preferred.

Suitable catalysts (accelerators) are for example: tertiary amines, their salts or quaternary ammonium compounds, for example benzyldimethylamine, 2,4,6-tris(dimethylaminomethyl)phenol, 1-methylimidazole, 2-ethyl-4-methylimidazole, 2-phenylimidazole, 4-aminopyridine and tripentylammonium phenolate; or alkali metal alcoholates, for example sodium hexanetriolate. The reaction (curing) of the mixtures according to the invention is advantageously performed within the temperature range of 50° to 300° C., preferably between 150° and 300° C.

The preferred curing accelerator is 2-phenylimidazole.

Curing can be performed, in a known manner, also in two or more stages, the first curing stage being carried out at low temperature and the subsequent curing at elevated temperature.

The curing process can if desired be performed also in two stages using a procedure in which the curing reaction is firstly prematurely interrupted or the first stage is carried out at only slightly elevated temperature, with the result that a still fusible and/or soluble, curable pre-condensate (so-called "B stage") is obtained from the imide component (a) and the epoxide component (b). A pre-condensate of this type can be used for example for producing "prepregs", moulding material or sinter powders.

The term "curing", in the way it is used here, signifies the transformation of the soluble, either liquid or fusible, epoxide resins into solid, insoluble and infusible, three-dimensional crosslinked products or materials, as a rule with simultaneous shaping into the form of moulded articles, such as cast shapes, pressed components and laminates, or into the form of impregnations, coatings, lacquer films or adhesive bonds.

Inert and stable substances, such as fillers, pigments, dyes and other additives, can obviously be added to the imides of the formula I before these are polymerised into crosslinked articles.

The imides of the formula (I) according to the invention, particularly those wherein n is 1, can be reacted for example with a sulfochloride of the formula $$R^4-SO_2Cl \qquad (V),$$

with cooling and in the presence of an HCl acceptor, to give the corresponding sulfonic esters, $R^4$ in the formula V being $C_1-C_6$-alkyl, $C_5-C_6$-cycloalkyl, $C_6-C_{10}$-aryl or $C_7-C_{12}$-alkaryl, and preferably methyl, phenyl or p-tolyl.

The reaction of compounds of the formula I with the sulfochlorides of the formula V is performed preferably with an equimolar ratio of the reactants in an inert solvent having a boiling point of below 200° C. Suitable solvents are for example aliphatic or alicyclic, optionally chlorinated hydrocarbons, and especially aromatic, optionally chlorinated hydrocarbons, such as chlorobenzene, xylene and particularly toluene. In order to neutralise the hydrochloric acid forming during the reaction, the reaction is carried out in the presence of an HCl-acceptor, preferably a tertiary amine, for example triethylamine, dimethylaniline, pyridine or lutidine. Since the reaction proceeds exothermically, cooling is applied to prevent the temperature of the reaction mixture from exceeding preferably 10° C.

The compounds obtained in this manner are liquid or low-melting solid substances. At elevated temperature, they release the corresponding sulfonic acid, $R^4SO_3H$, $R^4$ having the meaning defined in the foregoing, and are thus suitable as latent catalysts for the crosslinking of cationically polymerizable material. The radical of the compounds which remains after the cleavage of the sulfonic acid, owing to its polyfunctionality, becomes concomitantly incorporated into the end polymer. It is also possible to use a mixture of several of the above-described compounds as a catalyst.

Suitable cationically polymerisable materials for which the aforementioned sulfonic esters can be used as catalysts are, inter alia, substituted, unsaturated bicyclic imides, such as are described for example in the European Patent Application No. 0,105,024. The crosslinked polymers thus obtained are distinguished by excellent mechanical and thermal properties.

The production of some imides according to the invention, the properties thereof and the application of these imides are illustrated in the following Examples.

PRODUCTION EXAMPLES

Example 1

Methallylbicyclo[2.2.1]hept-5-ene-2,3-dicarboxylic acid-N-hydroxylimide 34.75 g of hydroxylamine hydrochloride are dissolved in water, and 109 g of methallylbicyclo[2.2.1]hept-5-ene-2,3-dicarboxylic anhydride are added. There are then added dropwise, with stirring, 40 g of 50% aqueous sodium hydroxide solution, and the mixture is refluxed for 1 hour. All volatile components are afterwards distilled off, the residue is taken up in toluene, the precipitated sodium chloride is filtered off, and the toluene is removed in a rotary evaporator (150° C., 2000 Pa). There are thus obtained 98.5 g of a highly viscous liquid (90% of theory), which is not distillable up to 200° C./2.5 Pa, since the product presumably is in the form of a dimer.

| $C_{13}H_{13}NO_2$ | Analysis calculated | found |
|---|---|---|
| % C | 71.23 | 71.08 |
| % H | 5.98 | 6.07 |
| % N | 6.39 | 6.51 |

Example 2

Allylbicyclo[2.2.1]hept-5-ene-2,3-dicarboxylic acid-N-(2'-hydroxyethyl)imide 760 g of allylbicyclo[2.2.1]hept-5-ene-2,3-dicarboxylic anhydride (isomeric mixture) are placed into the reaction vessel, and 227.55 g of monoethanolamine are added dropwise with stirring. The mixture is refluxed for 2 hours, and water and some excess monoethanolamine are distilled off until a temperature of 175° C. is reached. The pressure is then decreased to 2670 Pa. The temperature is lowered to 100° C. and the product is rectified at 4.9 Pa. At between 170° and 174° C., there distil over 712.4 g (77.3% of theory) of a pale yellow oil having the following characteristic values:

$n_{25}{}^D = 1.5344$ $\eta_{25} = 2.43$ Pa.s.

| | Analysis calculated | found |
|---|---|---|
| % C | 68.00 | 68.08 |
| % H | 6.93 | 7.06 |
| % N | 5.66 | 5.61 |

IR Spectrum: 1619 cm$^{-1}$ cyclic double bond; 1641 cm$^{-1}$ allyl group; 1697 cm$^{-1}$ carbonyl group; 1768 cm$^{-1}$ carbonyl in the cyclic imide; 3449 cm$^{-1}$ hydroxyl group.

The product obtained by the process is, like the starting material, a mixture of the 1 exo-, 6 exo-, 1 endo- and 6 endo-isomers.

Example 3

Allylbicyclo[2.2.1]hept-5-ene-2,3-dicarboxylic acid-N-(2',2'-dimethyl-3'-hydroxypropyl)imide 204 g of allylbicyclo[2.2.1]hept-5-ene-2,3-dicarboxylic anhydride (isomeric mixture) are reacted with 103 g of neopentanolamine at 120° C. for 4 hours, and the product is distilled. There is obtained between 169° and 172° C. at 2.53 Pa 268 g (92.7% of theory) of a yellow oil having a refractive index $n_{25}^D$ of 1.5190 and a viscosity of 6.21 Pa.s.

| | Analysis calculated | found |
|---|---|---|
| % C | 70.56 | 70.67 |
| % H | 8.01 | 8.13 |
| % N | 4.84 | 4.77 |
| % OH | 5.88 | 5.69 |

The hydroxyl-group content is determined by acetylation with acetic anhydride in pyridine.

Example 4

Allylbicyclo[2.2.1]hept-5-ene-2,3-dicarboxylic acid-N-[2'-(2''-hydroxyethoxy)ethyl]imide 120 g of allylbicyclo[2.2.1]hept-5-ene-2,3-dicarboxylic anhydride (isomeric mixture) are reacted at 140° C. with 67.9 g of diglycolamine; the mixture is heated to 200° C. and the pressure lowerd to 10.6 Pa. The yield is 142.6 g of a yellow oil having a viscosity of 1.55 Pa.s at 25° C. and an $n_{25}^D$ of 1.5230.

| | Analysis calculated | found |
|---|---|---|
| % C | 65.96 | 65.74 |
| % H | 7.27 | 7.39 |
| % N | 4.81 | 4.71 |
| % OH | 5.84 | 5.34 |

Example 5

Allylbicyclo[2.2.1]-hept-5-ene-2,3-dicarboxylic acid-N-(2',3'-dihydroxypropyl)imide 102 g of allylbicyclo[2.2.1]hept-5-ene-2,3-dicarboxylic anhydride are heated with 45.55 g of 2,3-dihydroxypropylamine to 200° C., and the pressure is lowered to 47 Pa. The yield is 138 g (96.5% of theory) of a highly viscous product having $\eta_{80}=605$ mPa.s and $n_{25}^D=1.5380$.

| | Analysis calculated | found |
|---|---|---|
| % C | 64.97 | 64.48 |
| % H | 6.91 | 7.02 |
| % N | 5.05 | 4.96 |
| % OH | 6.13 | 5.95 |

Example 6

Allylbicyclo[2.2.1]hept-5-ene-2,3-dicarboxylic acid-N-(4'-hydroxyphenyl)imide 408 g of an isomeric mixture of allylbicyclo[2.2.1-]hept-5-ene-2,3-dicarboxylic anhydride are heated with 238.26 g of 4-aminophenol to 200° C.; the pressure is lowered to 2.7 Pa and the mixture is held for 1 hour under these conditions. There are thus obtained 535 g of a red solid resin (87.7% of theory) having a glass transition temperature of 58° C.

| | Analysis calculated | found |
|---|---|---|
| % C | 73.20 | 72.43 |
| % H | 5.90 | 6.05 |
| % N | 4.89 | 4.90 |
| % OH | 5.76 | 5.38 |

Example 7

Allylbicyclo[2.2.1]hept-5-ene-2,3-dicarboxylic acid-N-(3'-hydroxyphenyl)imide

The procedure is carried out as in the previous Example 6 except that 3-aminophenol is used. There is obtained a reddish-brown solid resin having a glass transition temperature of 61° C.; yield 97.5% of theory.

| | Analysis calculated | found |
|---|---|---|
| % C | 73.20 | 72.56 |
| % H | 5.80 | 6.02 |
| % N | 4.74 | 5.97 |
| % OH | 5.76 | 5.66 |

Example 8

Allylmethylbicyclo[2.2.1]hept-5-ene-2,3-dicarboxylic acid-N-[4'-(4''-hydroxyphenylisopropylidene)phenyl]imide

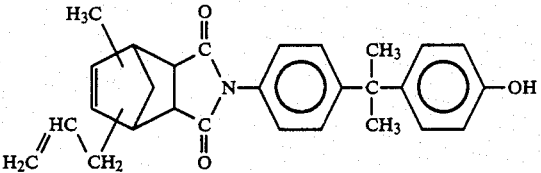

54 g of allylmethylbicyclo[2.2.1]hept-5-ene-2,3-dicarboxylic anhydride are reacted, at 200° C. and 2.5 Pa, with 56.74 g of 2-(4'-aminophenyl)-2-(4''-hydroxyphenyl)propane. The yield is 100.5 g of a dark-brown solid resin (97.3% of theory) having a glass transition temperature of 100° C.

| | Analysis calculated | found |
|---|---|---|
| % C | 78.45 | 78.15 |
| % H | 6.58 | 6.54 |
| % N | 3.39 | 3.16 |

Example 9

Allylbicyclo[2.2.1]hept-5-ene-2,3-dicarboxylic acid-N-hydroxylimide

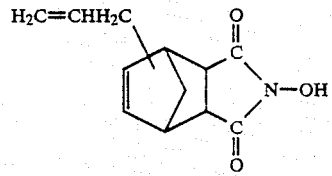

139 g (2 mols) of hydroxylamine hydrochloride are dissolved in 200 ml of water; there are then added 408 g (2 mols) of allylbicyclo[2.2.1]hept-5-ene-2,3-dicarboxylic anhydride (produced according to Example 1 of the U.S. Pat. No. 3,105,839), and 160 g of 50% aqueous sodium hydroxide solution are subsequently introduced dropwise with vigorous stirring. The mixture is afterwards refluxed for 1 hour; the water and traces of oily constituents are distilled off, the residue is taken up in toluene, the sodium chloride is filtered off, and the toluene is removed in a rotary evaporator at 150° C. and 2000 Pa. There remain 402.6 g of the product (91.5% of theory) in the form of a light-brown viscous liquid having a viscosity of 1.28 Pa.s at 80° C.

| Analysis | | |
|---|---|---|
| | calculated | found |
| % C | 65.74 | 65.34 |
| % H | 5.98 | 6.02 |
| % N | 6.39 | 6.40 |

APPLICATION EXAMPLES

Examples I–V

The imides and epoxide compounds listed in the following Table are in each case melted together at about 150° C.; 2-phenylimidazole is then added as the catalyst, degassing is performed in vacuo, and the resin melts are poured into plate moulds having dimensions of 120×120×4 mm³. The material is thereupon cured for 3 hours at 200° C., for 3 hours at 220° C. and for 12 hours at 250° C. to thus obtain perfectly satisfactory, dark-red-coloured, tough-hard plates, which are sawn up into test bars. The properties shown in the Table are measured on these test specimens.

TABLE

| Example No. | | I | II | III | IV | V |
|---|---|---|---|---|---|---|
| product from Production Example No. | | 6 | 7 | 8 | 7 | 8 |
| amount (g) | | 60 | 60 | 60 | 60 | 60 |
| polyglycidylated pheno-formaldehyde novolak[a] | (g) | 35.7 | 35.7 | — | — | — |
| bisphenol-A diglycidyl ether[b] | (g) | — | — | 32.5 | 32.5 | 27.2 |
| 2-phenylimidazole (mg) | | 95.6 | 95.6 | 92.5 | 92.5 | 87.2 |
| flexural strength (ISO 178) (N/mm²) | | 118 | 70.9 | — | 85.2 | — |
| after 14 days in water at 71° C. (N/mm²) | | 42.2 | 56.4 | — | 48.6 | — |
| edge-fibre elongation (%) | | 5.1 | 1.95 | — | 2.2 | — |
| after 14 days in water at 71° C. (%) | | 1.5 | 1.59 | — | 1.5 | — |
| impact bend strength (ISO 179) (kJ/m²) | | 23.2 | 4.3 | — | 6.3 | — |
| after 14 days in water at 71° C. (kJ/m²) | | 20.4 | 4.7 | — | 6.5 | — |
| water absorption after 14 days at 71° C. (%) | | 3.2 | 2.7 | — | 3.1 | — |
| glass transition temperature (°C.) (Mettler TA 2000) | | 222.5 | 193 | 204 | 188 | 186 |

[a] epoxide content 5.7 equivalents/kg
[b] epoxide content 5.3 equivalents/kg are then added, and stirring is maintained until a homogeneous solution is formed. The solution is cooled to 0° C. and, with vigorous stirring and external cooling, 324.7 g of benzenesulfonyl chloride are added dropwise in such a manner that the temperature of the reaction mixture remains between 5° and 10° C. The mixture is stirred overnight at room temperature, water is added, the pH value is adjusted to 5 with concentrated hydrochloric acid, and the mixture is subsequently washed twice with water at 75° C. After separation of the aqueous phase, the product is dried over $Na_2SO_4$, filtered, and concentrated in a rotary evaporator at 110° C. and 2000 Pa. The yield is 471 g of a viscous liquid which crystallises on standing (m.p.=97.99° C.).

| Elementary analysis | | |
|---|---|---|
| | calculated | found |
| % C | 60.16 | 60.35 |
| % H | 4.77 | 4.85 |
| % N | 3.90 | 3.90 |
| % S | 8.92 | 8.59 |

IR Spectrum (cm$^{-1}$): 575.4, 685.5 and 736.2 aryl; 1195 and 1398 —$SO_2O$—; 1620 cycl. double bond; 1640 allyl double bond; 1742 carbonyl.

(b) Use as catalyst for cationic polymerisation

The resin given below is cured in the presence of the sulfonyloxyimide produced under (a), which acts as a latent catalyst.

Resin: Bis[4-(allylbicyclo[2.2.1]hept-5-ene-2,3-dicarboxylic acid-imidophenyl)methane], produced according to Example 11 of the European Patent Application No. EP-A 0,105,024.

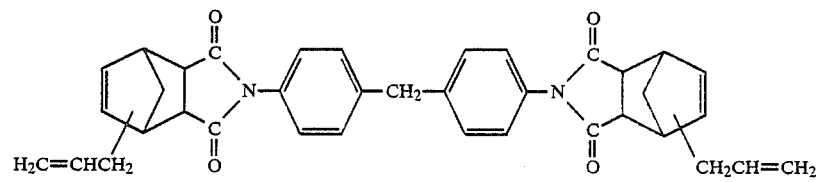

Example VI (a) Production of allylbicyclo[2.2.1]hept-5-ene-2,3-dicarboxylic acid-N-benzenesulfonyloxyimide The product obtained according to Example 9 is dissolved in 1 liter of toluene; 222.8 g of triethylamine To the resin is added 1% of the catalyst, the mixture is heated, evacuated, poured into steel moulds having dimensions of 150×150×4 mm³, and cured for 2 hours at 190° C. and for 2 hours at 250° C.

The cured product has the following characteristics:

| | |
|---|---|
| flexural strength (ISO 178) | 99.0 N/mm² |
| edge-fibre elongation | 3.4% |
| impact bend strength (ISO 179) | 6.1 kJ/m² |
| glass transion temperature (Mettler TA 2000) | 280° C. |

What is claimed is:

1. An imide of the formula I

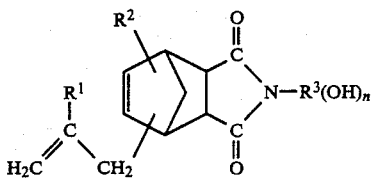
(I)

wherein $R^1$ and $R^2$ independently of one another are each hydrogen or methyl, n is 1, 2 or 3, and $R^3$ is a direct bond with n being 1, or $C_2$–$C_{20}$-alkylene,

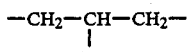

when n is 2,

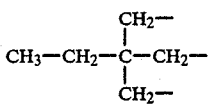

when n is 2,

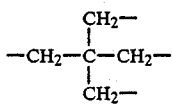

when n is 3, $-CH_2-CH_2[OCH_2CH_2]_{\overline{m}}$ when n is 1 or $-CH_2CH_2CH_2[OCH_2CH_2CH_2]_{\overline{m}}$ when n is 1 with m=1–10, $C_5$–$C_{20}$ cycloalkylene or bis($C_5$–$C_{20}$ cycloalkylene) $C_1$–$C_3$ alkane having the OH(s) substituted on the cycloalkylene ring, a $C_6$–$C_{10}$ aromatic radical or said $C_6$–$C_{10}$ aromatic radical substituted by $C_1$–$C_4$ alkyl, or a group of the formula II

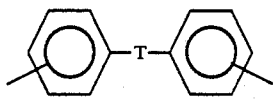
(II)

wherein T is methylene, isopropylidene, CO, O, S or $SO_2$; the OH groups being bound to different C atoms of $R^3$.

2. An imide of the formula I according to claim 1 wherein $R^1$ and $R^2$ are each hydrogen.

3. An imide of the formula I according to claim 1 wherein $R^3$ is a direct bond, a group $-C_rH_{2r}-$ in which r is 2-6, a group $-CH_2CH_2[OCH_2CH_2]_m$ in which m is 2 or 1,

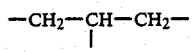

a mononuclear, divalent, cycloalkylene radical having 5–8 C atoms, a divalent $C_6$–$C_{10}$-aromatic radical, or a group of the formula II in which T is O, $SO_2$, methylene or isopropylidene.

4. An imide of the formula I according to claim 1 wherein $R^3$ is a direct bond, or the radical

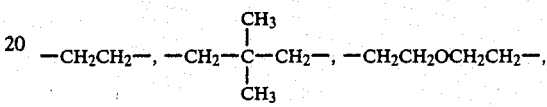

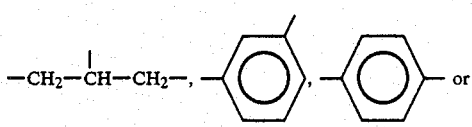

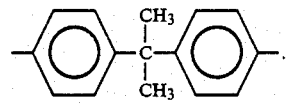

5. A imide of the formula I according to claim 1 wherein $R^3$ is a direct bond, ethylene or 1,4-phenylene.

6. An imide of the formula I according to claim 1 wherein $R^1$ is methyl, $R^2$ is hydrogen, $R^3$ is a direct bond and n is 1.

7. An imide of the formula I according to claim 1 wherein $R^1$ and $R^2$ are each hydrogen, and $R^3(OH)_n$ is 2-hydroxyethyl.

8. An imide of the formula I according to claim 1 wherein $R^1$ and $R^2$ are each hydrogen, and $R^3(OH)_n$ is 2,2-dimethyl-3-hydroxypropyl.

9. An imide of the formula I according to claim 1 wherein $R^1$ and $R^2$ are each hydrogen, and $R^3(OH)_n$ is 2-(2'-hydroxyethoxy)ethyl.

10. An imide of the formula I according to claim 1 wherein $R^1$ and $R^2$ are each hydrogen, and $R^3(OH)_n$ is 2,3-dihydroxypropyl.

11. An imide of the formula I according to claim 1 wherein $R^1$ and $R^2$ are each hydrogen, and $R^3(OH)_n$ is 4-hydroxyphenyl.

12. An imide of the formula I according to claim 1 wherein $R^1$ and $R^2$ are each hydrogen, and $R^3(OH)_n$ is 3-hydroxyphenyl.

13. An imide of the formula I according to claim 1 wherein $R^1$ is hydrogen, $R^2$ is methyl, and $R^3(OH)_n$ is 4-(4'-hydroxyphenylisopropylidene)phenyl.

* * * * *